US008846662B2

(12) United States Patent
Hoernecke

(10) Patent No.: US 8,846,662 B2
(45) Date of Patent: Sep. 30, 2014

(54) BENZODIAZEPINE AND/OR PHARMACEUTICAL COMPOSITION COMPRISING BENZODIAZEPINE DERIVATIVES

(75) Inventor: Rainer Hoernecke, Munich (DE)

(73) Assignee: Dr. Franz Koehler Chemie GmbH, Bernsheim (DE)

( * ) Notice: Subject to any disclaimer, the term of this patent is extended or adjusted under 35 U.S.C. 154(b) by 800 days.

(21) Appl. No.: 12/863,353

(22) PCT Filed: Jan. 15, 2009

(86) PCT No.: PCT/DE2009/000042
§ 371 (c)(1),
(2), (4) Date: Mar. 27, 2011

(87) PCT Pub. No.: WO2009/089826
PCT Pub. Date: Jul. 23, 2009

(65) Prior Publication Data
US 2011/0263576 A1    Oct. 27, 2011

(30) Foreign Application Priority Data
Jan. 16, 2008    (DE) .................. 10 2008 004 694

(51) Int. Cl.
*A61K 31/55*    (2006.01)

(52) U.S. Cl.
USPC ............................ 514/220; 514/221; 424/400

(58) Field of Classification Search
USPC ................................... 514/220, 221; 424/400
See application file for complete search history.

(56) References Cited

U.S. PATENT DOCUMENTS

| | | | | |
|---|---|---|---|---|
| 4,371,516 A * | 2/1983 | Gregory et al. | ............... | 424/485 |
| 4,832,952 A | 5/1989 | Hersh | | |
| 2005/0004234 A1 * | 1/2005 | Bell et al. | ...................... | 514/731 |
| 2006/0183722 A1 * | 8/2006 | Mazess et al. | ................ | 514/167 |
| 2008/0138383 A1 * | 6/2008 | Bortz et al. | .................... | 424/434 |

FOREIGN PATENT DOCUMENTS

| | | | |
|---|---|---|---|
| DE | 40 39 602 A1 | 6/1992 | |
| DE | 198 51 777 A1 | 5/2000 | |

OTHER PUBLICATIONS

Strickley (Pharmaceutical Research, 21, 2, 2004).*
Lau et al. (Int J of Pharmaceutics, 54, 1989, 171-174).*
Liu et al. (Drugs, 63, 8, 2003, 755-767).*
Liu et al. (Luminescence, 2003, 18, 245-248).*
Friedrich et al. (E J of Pharmaceutics and Biopharmaceutics, 62, 2006, 171-77).*
Oswald (British Medical Journal, 284, Mar. 20, 1982, 860-863).*
IB, International Search Report, PCT/DE2009/000042, Dated May 20, 2009.
Bittner B et al: "Impact of Solutol HS 15 on the pharmacokinetic behavior of midazolam upon intravenous administration to male Wistar rats" European Journal of Pharmaceutics and Biopharmaceutics, Elsevier Science Publishers B.V., Amsterdam, NL, vol. 56, No. 1, Jul. 1, 2003, ISSN: 0939-6411 paragraph [02.2].
Colpaert F C et al: "Discriminative stimulus properties of benzodiazepines, barbiturates and pharmacologically related drugs; Relation to some intrinsic and anticonvulsant effects" European Journal of Pharmacology, Elsevier BV, NL, vol. 37, No. 1, May 1, 1976, pp. 113-123, XP025812190 ISSN: 0014-2999 [retreived on May 1, 1976] paragraph [02.3].
Menton et al: "Serotonergic drugs, benzodiazepines and baclofen block muscimol-induced myoclonic jerks in a strain of mice" European Journal of Pharmacology, Elsevier BV, NL, vol. 73, No. 2-3; Jul. 17, 1981, pp. 155-161, XP0255558242, ISSN: 0014-2999 [retreived on Jul. 17, 1981] p. 156, col. 1.
Simiand J et al: "Comparative study in mice of tetrazeoam and other centrally active skeletal muscle relaxants." Archives Internationales De Pharmacodynamie Et De Therapie Jan.-Feb. 1989, vol. 297, Jan. 1989, pp. 272-285, XP009116721, ISSN:0301-4533, p. 275, paragraph 2, p. 276, paragraph 3-paragraph 4, table 6 p. 281.
Zarrindast M R et al: "Involvement of dopaminergic receptor subtypes in straub tail behaviour in mice" General Pharmacology, Pergamon Press, Oxford, GB, vol. 24, No. 1, Jan. 1, 1993, pp. 127-130, XP023819124, ISSN: 0306-3623 [retreived on Jan. 1, 1993] the whole document.
Solutol HS 15, Marcrogol 15 Hydroxystearate as a nonionic solubilizer for injection solutions, BASF, Jul. 2003.
Physiochemical Properties of Solutol HS 15 and its Solubilizates, BASF, Nov. 1998, p. 6-7.
T. Reinhart and K. Bauer, Untersuchungen zum Hamolyse- und Solubilisations-verhalten einiger nichtionischer polyrnerer Tensidklassen, in: Die Pharmazie, 1995, vol. 50, p. 403-047, ISSN 0031-7144.

* cited by examiner

*Primary Examiner* — Uma Ramachandran
(74) *Attorney, Agent, or Firm* — Nexsen Pruet, LLC

(57) ABSTRACT

The invention relates to a pharmaceutical composition characterized in that it comprises a benzodiazepine and/or benzodiazapine derivative, and a non-ionic solubilizer, and induces in said combination an analogous effect to an opiate, described as a Straub phenomenon.

9 Claims, No Drawings

BENZODIAZEPINE AND/OR PHARMACEUTICAL COMPOSITION COMPRISING BENZODIAZEPINE DERIVATIVES

The invention relates to a pharmaceutical composition containing benzodiazepine and/or benzodiazepine derivatives.

Lorazepam (INN) is a 7-chloro-5-(o-chlorophenyl)-1,3-dihydro-3-hydroxy-2H-1,4-benzodiazepin-2-one (WHO), i.e., 9-chloro-6-(2-chlorophenyl)-4-hydroxy-2,5-diazabicyclo[5.4.0]undeca-5,8,10,12-tetraen-3-one (systematic IUPAC name).

Lorazepam is a psychotropic substance from the 1,4-benzodiazepine class with anxiolytic, stress-reducing and agitation-reducing properties as well as sedative and hypnotic effects. In addition, lorazepam also has anticonvulsant and muscle relaxant effects.

Lorazepam has a very high affinity for very specific bonding sites in the central nervous system. These bonding sites are in close functional relation to the receptors of the inhibitory neurotransmitter gamma-aminobutyric acid (GABA). After binding to the receptor, lorazepam enhances the GABAergic inhibition of the activity of the downstream neurons.

Therapeutic formulations containing lorazepam administered intravenously and intramuscularly have been approved for therapeutic use in Germany since 1988 for basic sedation before and during diagnostic and surgical procedures, to reduce anxiety and stress, including the creation of amnestic effects, for initiating treatment of severe neurotic anxiety symptoms and extreme phobias, for adjuvant treatment of severe anxiety and agitation states in psychoses and depression and for treatment of status epilepticus.

Lormetazepam (INN) is 7-chloro-5-(o-chlorophenyl)-1,3-dihydro-3-hydroxy-2H-1,4-benzo-diazepin-2-one (WHO), i.e., 9-chloro-6-(2-chlorophenyl)-4-hydroxy-2-methyl-2,5-diazabicyclo-[5.4.0]undeca-5,8,10,12-tetraen-3-one (systematic IUPAC name).

Lormetazepam is a psychotropic substance from the 1,4-benzodiazepine class with sedative and hypnotic effects as well as anxiolytic effects in addition to reducing stress and agitation. Furthermore, lormetazepam has central muscle relaxant and anticonvulsant effects.

Lormetazepam has a very high affinity for specific binding sites in the central nervous system. These binding sites are in close functional connection to the receptors of GABA, the inhibitory neurotransmitter.

In Germany, intravenously administered therapeutic compositions containing lormetazepam have been approved for treatment of acute anxiety states, for preoperative anxiolysis, for premedication for narcoses in surgical procedures, and for sedation in intensive care medicine since 1993.

Oxazepam (INN) is a 9-chloro-4-hydroxy-6-phenyl-2,5-diazabicyclo[5.4.0]undeca-5,8,10,12-tetraen-3-one (systematic IUPAC name).

Oxazepam is a psychotropic substance from the 1,4-benzodiazepine class with anxiolytic, stress-reducing and agitation-reducing properties as well as sedative and hypnotic effects. Furthermore, in high doses oxazepam has anticonvulsant and muscle relaxant effects.

Oxazepam binds with a moderately strong affinity to specific receptors in the central nervous system, the benzodiazepine receptors of the GABAergic transmitter system. After binding to the benzodiazepine receptor, oxazepam enhances the inhibiting effect of the GABAergic transmission.

Intravenously administered pharmaceutical compositions containing oxazepam have not previously been available on the market, but this substance in an oral dosage form is an approved pharmaceutical drug in many countries. In this form, it is approved for symptomatic treatment of acute and chronic anxiety, stress and agitation states, for supplementary short-term treatment of severe anxiety, stress and agitation states and for symptomatic treatment of sleeping disorders.

Macrogol-15-hydroxystearate (monograph name, Ph. Eur.), with the brand name Solutol® HS 15, is a nonionic solvent for injection solutions, consisting of a mixture of mainly mono- and diesters of 12-hydroxystearic acid and macrogols (15 mol ethylene oxide and 1 mol 12-hydroxystearic acid).

Macrogol-15-hydroxystearate comprises polyglycol mono- and diesters of 12-hydroxystearic acid (lipophilic portion) and approx. 30% free polyethylene glycol (hydrophilic portion).

Macrogol-15-hydroxystearate dissolves in water, ethanol and 2-propanol to form a clear solution; the solubility in water declines at higher temperatures.

Macrogol-15-hydroxystearate has a high chemical stability. However, it may be separated physically into a liquid phase and a solid phase with prolonged application of heat. This can be reversed by subsequent homogenization.

Aqueous solutions of macrogol-15-hydroxystearate can be autoclaved at 121° C. There may be a slight decline in pH in this process and phase separation may even occur. The latter can be reversed by shaking the hot solution.

Aqueous solutions of macrogol-15-hydroxystearate can be stabilized by adding the usual preservatives in drugs.

Macrogol-15-hydroxystearate also has a good solubilizing power, autoclavability, and a good stability in aqueous solutions plus a favorable toxic profile, for example, a low hemolytic activity.

Macrogol-15-hydroxystearate is approved for parenteral administration.

Neither benzodiazepine nor benzodiazepine derivatives nor nonionic solubilizers have an opiate effect.

DE 4039602 A1 describes polymeric compounds which may be used as solubilizers for sparingly soluble pharmaceutical substances, for use in pharmaceutical products for intravenous injections. Macrogol-15-hydroxystearate is also mentioned there as a nonionic solubilizer.

US 2006/6183722 A1 also describes lipophilic pharmaceutical substances having a low water solubility and the problems associated with that in parenteral administration. Pharmaceutical products suitable for parenteral administration are obtained by using nonionic surfactants as solubilizers. Benzodiazepines are also mentioned among the active lipophilic ingredients. Suitable solubilizers that are mentioned include nonionic solubilizers such as macrogol.

However, none of the publications cited above mention an opiate-like effect of the individual substances or combinations thereof.

The object of the present invention is to provide a pharmaceutical composition which induces an opiate-like effect.

This object is surprisingly achieved by a pharmaceutical composition, which is characterized in that it comprises a benzodiazepine and/or benzodiazepine derivates as well as a nonionic solubilizer, and in this combination, it induces an opiate-like effect that is described as Straub's phenomenon.

In a preferred embodiment of the present invention, the nonionic solubilizer is macrogol-15-hydroxystearate.

In an especially preferred embodiment of the present invention, the pharmaceutical composition is characterized in that it contains lorazepam and/or lormetazepam and/or oxazepam and/or a derivative thereof. In the case of benzodiazepine and/or benzodiazepine derivatives, their pharmaceutically tolerable salts may also be used.

Furthermore, the use of the nonionic solubilizer in an amount of 2-45 wt % is especially preferred.

When using lorazepam, in general the nonionic solubilizer is preferably used in an amount of 2% to 10% (w/w), especially preferably in an amount of 3% (w/w).

When using lormetazepam, the nonionic solubilizer is preferably used in an amount of 3% to 10% (w/w), especially preferably in an amount of 4% (w/w).

When using oxazepam, the nonionic solubilizer is preferably used in an amount of 10% to 25% (w/w), especially preferably in an amount of 5% (w/w).

Induction of the Straub's phenomenon by various solvents and by lormetazepam in various solvents is summarized below.

| Study | No. | Medication | Dose mg/mL | Species | Sex | Weight 1/g | Weight 7/g | Behavior | Test Passed | Straub |
|---|---|---|---|---|---|---|---|---|---|---|
| GMF-LOR03tox | 1 | LOR AL | 0.4/1 | Mouse NMRI | M | 25 | 29 | normal | yes | no |
| GMF-LOR03tox | 2 | LOR AL | 0.4/1 | Mouse NMRI | M | 25 | 29 | normal | yes | no |
| GMF-LOR03tox | 3 | LOR AL | 0.4/1 | Mouse NMRI | M | 25 | 31 | normal | yes | no |
| GMF-LOR03tox | 4 | LOR AL | 0.4/1 | Mouse NMRI | M | 28 | 29 | normal | yes | no |
| GMF-LOR03tox | 5 | LOR AL | 0.4/1 | Mouse NMRI | M | 24 | 31 | normal | yes | no |
| GMF-LOR03tox | 1 | LOR IL | 0.4/1 | Mouse NMRI | M | 25 | 31 | normal | yes | no |
| GMF-LOR03tox | 2 | LOR IL | 0.4/1 | Mouse NMRI | M | 26 | 31 | normal | yes | no |
| GMF-LOR03tox | 3 | LOR IL | 0.4/1 | Mouse NMRI | M | 26 | 29 | normal | yes | no |
| GMF-LOR03tox | 4 | LOR IL | 0.4/1 | Mouse NMRI | M | 27 | 32 | normal | yes | no |
| GMF-LOR03tox | 5 | LOR IL | 0.4/1 | Mouse NMRI | M | 25 | 29 | normal | yes | no |
| GMF-LOR03tox | 1 | LOR LF | 0.4/1 | Mouse NMRI | M | 24 | 29 | normal | yes | no |
| GMF-LOR03tox | 2 | LOR LF | 0.4/1 | Mouse NMRI | M | 25 | 31 | normal | yes | no |
| GMF-LOR03tox | 3 | LOR LF | 0.4/1 | Mouse NMRI | M | 24 | 31 | normal | yes | no |
| GMF-LOR03tox | 4 | LOR LF | 0.4/1 | Mouse NMRI | M | 26 | 32 | normal | yes | no |
| GMF-LOR03tox | 5 | LOR LF | 0.4/1 | Mouse NMRI | M | 25 | 29 | normal | yes | no |
| GMF-LOR03tox | 1 | LOR LV | 0.4/1 | Mouse NMRI | M | 26 | 29 | normal | yes | no |
| GMF-LOR03tox | 2 | LOR LV | 0.4/1 | Mouse NMRI | M | 25 | 32 | normal | yes | no |
| GMF-LOR03tox | 3 | LOR LV | 0.4/1 | Mouse NMRI | M | 26 | 31 | normal | yes | no |
| GMF-LOR03tox | 4 | LOR LV | 0.4/1 | Mouse NMRI | M | 26 | 29 | normal | yes | no |
| GMF-LOR03tox | 5 | LOR LV | 0.4/1 | Mouse NMRI | M | 25 | 29 | normal | yes | no |
| GMF-LOR03tox | 1 | LOR SL | 0.4/1 | Mouse NMRI | M | 20 | 26 | normal | yes | no |
| GMF-LOR03tox | 2 | LOR SL | 0.4/1 | Mouse NMRI | M | 21 | 26 | normal | yes | no |
| GMF-LOR03tox | 3 | LOR SL | 0.4/1 | Mouse NMRI | M | 22 | 27 | normal | yes | no |
| GMF-LOR03tox | 4 | LOR SL | 0.4/1 | Mouse NMRI | M | 21 | 29 | normal | yes | no |
| GMF-LOR03tox | 5 | LOR SL | 0.4/1 | Mouse NMRI | M | 20 | 28 | normal | yes | no |
| GMF-LOR04tox | 1 | SO HS 15 | 40/1 | Mouse NMRI | M | 21 | 27 | normal | yes | no |
| GMF-LOR04tox | 2 | SO HS 15 | 40/1 | Mouse NMRI | M | 20 | 28 | normal | yes | Straub |
| GMF-LOR04tox | 3 | SO HS 15 | 40/1 | Mouse NMRI | M | 21 | 29 | normal | yes | no |
| GMF-LOR04tox | 4 | SO HS 15 | 40/1 | Mouse NMRI | M | 21 | 27 | normal | yes | no |
| GMF-LOR04tox | 5 | SO HS 15 | 40/1 | Mouse NMRI | M | 20 | 28 | normal | yes | no |
| GMF-LOR04tox | 1 | SO HS 15 | 400/1 | Mouse NMRI | M | 22 | 30 | normal | yes | no |
| GMF-LOR04tox | 2 | SO HS 15 | 400/1 | Mouse NMRI | M | 20 | 28 | normal | yes | no |
| GMF-LOR04tox | 3 | SO HS 15 | 400/1 | Mouse NMRI | M | 23 | 30 | normal | yes | no |
| GMF-LOR04tox | 4 | SO HS 15 | 400/1 | Mouse NMRI | M | 21 | 29 | normal | yes | no |
| GMF-LOR04tox | 5 | SO HS 15 | 400/1 | Mouse NMRI | M | 20 | 28 | normal | yes | no |

-continued

| Study | No. | Medication | Dose mg/mL | Species | Sex | Weight 1/g | Weight 7/g | Behavior | Test Passed | Straub |
|---|---|---|---|---|---|---|---|---|---|---|
| GMF-LOR04tox | 1 | LOR WL | 0.2/1 | Mouse NMRI | M | 19 | 25 | normal | yes | yes |
| GMF-LOR04tox | 2 | LOR WL | 0.2/1 | Mouse NMRI | M | 20 | 27 | normal | yes | yes |
| GMF-LOR04tox | 3 | LOR WL | 0.2/1 | Mouse NMRI | M | 20 | 26 | normal | yes | yes |
| GMF-LOR04tox | 4 | LOR WL | 0.2/1 | Mouse NMRI | M | 19 | 26 | normal | yes | yes |
| GMF-LOR04tox | 5 | LOR WL | 0.2/1 | Mouse NMRI | M | 21 | 29 | normal | yes | yes |
| GMF-LOR04tox | 1 | LOR WL | 0.2/1 | Mouse NMRI | F | 19 | 25 | normal | yes | yes |
| GMF-LOR04tox | 2 | LOR WL | 0.2/1 | Mouse NMRI | F | 18 | 24 | normal | yes | yes |
| GMF-LOR04tox | 3 | LOR WL | 0.2/1 | Mouse NMRI | F | 18 | 26 | normal | yes | yes |
| GMF-LOR04tox | 4 | LOR WL | 0.2/1 | Mouse NMRI | F | 19 | 25 | normal | yes | yes |
| GMF-LOR04tox | 5 | LOR WL | 0.2/1 | Mouse NMRI | F | 18 | 27 | normal | yes | yes |
| GMF-PG50tox | 1 | PG 50% | 125/0.25 | Mouse NMRI | M | 20 | 26 | normal | yes | no |
| GMF-PG50tox | 2 | PG 50% | 125/0.25 | Mouse NMRI | M | 19 | 26 | normal | yes | no |
| GMF-PG50tox | 3 | PG 50% | 125/0.25 | Mouse NMRI | M | 20 | 26 | normal | yes | no |
| GMF-PG50tox | 4 | PG 50% | 125/0.25 | Mouse NMRI | M | 21 | 27 | normal | yes | no |
| GMF-PG50tox | 5 | PG 50% | 125/0.25 | Mouse NMRI | M | 20 | 25 | normal | yes | no |
| GMF-LOR04tox | 1 | NOCTAMID | 0.05/1 | Mouse NMRI | M | 18 | 24 | normal | yes | no |
| GMF-LOR04tox | 2 | NOCTAMID | 0.05/1 | Mouse NMRI | M | 20 | 25 | normal | yes | no |
| GMF-LOR04tox | 3 | NOCTAMID | 0.05/1 | Mouse NMRI | M | 20 | 23 | normal | yes | no |
| GMF-LOR04tox | 4 | NOCTAMID | 0.05/1 | Mouse NMRI | M | 19 | 26 | normal | yes | no |
| GMF-LOR04tox | 5 | NOCTAMID | 0.05/1 | Mouse NMRI | M | 20 | 27 | normal | yes | no |
| GMF-LOR04tox | 1 | LOR WL | 0.4/1 | Mouse NMRI | M | 20 | 27 | normal | yes | yes |
| GMF-LOR04tox | 2 | LOR WL | 0.4/1 | Mouse NMRI | M | 21 | 28 | normal | yes | yes |
| GMF-LOR04tox | 3 | LOR WL | 0.4/1 | Mouse NMRI | M | 20 | 26 | normal | yes | yes |
| GMF-LOR04tox | 4 | LOR WL | 0.4/1 | Mouse NMRI | M | 19 | 26 | normal | yes | yes |
| GMF-LOR04tox | 5 | LOR WL | 0.4/1 | Mouse NMRI | M | 20 | 27 | normal | yes | yes |
| GMF-LOR04tox | 1 | LOR WL | 0.4/1 | Mouse NMRI | F | 19 | 26 | normal | yes | yes |
| GMF-LOR04tox | 2 | LOR WL | 0.4/1 | Mouse NMRI | F | 18 | 26 | normal | yes | yes |
| GMF-LOR04tox | 3 | LOR WL | 0.4/1 | Mouse NMRI | F | 20 | 27 | normal | yes | yes |
| GMF-LOR04tox | 4 | LOR WL | 0.4/1 | Mouse NMRI | F | 19 | 27 | normal | yes | yes |
| GMF-LOR04tox | 5 | LOR WL | 0.4/1 | Mouse NMRI | F | 19 | 26 | normal | yes | yes |

Abbreviations:
LOR AL: Lormetazepam/Abbolipid
LOR IL: Lormetazepam/Intralipid
LOR LF: Lormetazepam/Lipofundin
LOR SL: Lormetazepam/Salvilipid
SO HS 15: Macrogol-15-hydroxystearate
LOR WL: Lormetazepam/Macrogol-15-hydroxystearate
NOCTAMID: Lormetazepam/propylene glycol 50%
PG 50%: Propylene glycol 50%
NMRI: Naval Medical Research Institute
F: Female
M: Male
Weight 1/g: Weight in grams on day 1 before administration of the respective medication
Weight 7/g: Weight in grams on day 7 (end of the study)
Straub: Induction of Straub's phenomenon In addition to the existence of the inventive pharmaceutical composition in the form of a solution or in the form of a gel, another preparation form is also possible.

In experiments with benzodiazepines dissolved in macrogol-15-hydroxystearate, the so-called Straub's phenomenon surprisingly occurred shortly after the injection. This effect persisted until the animals fell asleep due to the medication.

Lorazepam 0.03-0.05 mg in 0.2 mL i.v./mouse (weight approx. 20 g)

Lormetazepam 0.03-0.05 mg in 0.2 mL i.v./mouse (weight approx. 20 g)

Oxazepam 0.16-0.24 mg in 0.2 mL i.v./mouse (weight approx. 20 g)

Straub's phenomenon, also known as the mouse tail phenomenon or Straub's tail reaction (STR), is manifested in an S-shaped dorsal flexion of the tail and a protrusion of the perineum which is caused by the contraction of the sacrococcygeus muscle.

The occurrence of this phenomenon was unexpected because previously this had been observed only after injection of morphine or morphine analogs. Therefore, Straub's phenomenon had previously served as a reliable qualitative and semi-quantitative sign of a peripheral morphine effect.

The morphine reaction is induced by stimulation of the motor innervation on the level of the lumbosacral spine. Morphine acts on lumbosacral nerve cells and on descending nerve endings via the anterior horn of the spinal cord.

It should be pointed out in particular that Straub's phenomenon does not occur when the nonionic solubilizer is administered alone or when benzodiazepine and/or benzodiazepine derivatives are administered with other solvents, and in particular not when benzodiazepine and/or benzodiazepine derivatives are administered with an oil-in-water emulsion as the solvent (EP 0682943 A1) but instead it occurs only with the inventive combination as mentioned above.

The mouse tail phenomenon is described, for example, by Zarrindast M R, Alaei-Nia K, Shafizadeh M, On the Mechanism of Tolerance to Morphine-Induced Straub Tail Reaction in Mice, Pharmacol Biochem Behav. 2001 July-August; 69(3-4): 419-24 and Zarrindast M R, Ghadimi M, Ramezani-Tehrani B, Sahebgharani M., Effect of GABA Receptor Agonists or Antagonists on Morphine-Induced Straub Tail in Mice, International Journal of Neuroscience 2006, 116: 963-973.

The inventive pharmaceutical composition solves the problem presented here in an excellent manner.

The surprising observation on which the invention is based means that the respective active ingredient in combination with the nonionic solubilizer has a spectrum of effect which goes beyond that of benzodiazepine and/or benzodiazepine derivatives.

This pharmaceutical composition is especially suitable for applications in anesthesia, intensive care medicine, pain therapy or neurology/psychiatry.

The invention therefore also relates to a pharmaceutical composition comprising benzodiazepine and/or benzodiazepine derivatives as well as a nonionic solubilizer for use in anesthesia, intensive care medicine, pain therapy and neurology/psychiatry.

Accordingly, this pharmaceutical composition is also suitable for administration to the animal body.

General Preparation of an Injection Solution/Infusion Solution

According to one preparation procedure, the pharmaceutical composition containing the benzodiazepine and/or benzodiazepine derivatives can be prepared as described below.

The solubilizer macrogol-15-hydroxystearate is regulated at a temperature of 40-60° C. in a container equipped with a stirrer. Then the active ingredient, which is readily soluble therein, is added and dissolved while stirring. A clear solution is obtained after 15 to 30 minutes at a temperature of 50° C. (±10° C.).

The clear solution is then stirred into hot water for injection at 50-60° C. To prevent separation when added, the two phases should preferably be at a temperature of 55±5° C. Next the batch is cooled to 20-30° C. while stirring. After filling ampoules or vials with the injection solution, it may be autoclaved.

The invention is explained in greater detail below on the basis of examples.

EXAMPLE 1

400 g macrogol-15-hydroxystearate is melted. At a temperature of 50° C., 2.0 g lorazepam is added and dissolved while stirring. The clear solution is added while stirring to water for injection (WFI) according to Ph. Eur. (approx. 8 liters) previously heated to 50° C. Next the mixture is diluted to exactly 10 liters using water for injection to obtain an active ingredient concentration of 0.2 mg/mL.

The solution is cooled and sterile-filtered. Next glass ampoules are filled with 10 mL of the solution each and sterilized at 121° C. according to Ph. Eur. Each ampoule prepared in this way thus contains the desired therapeutic dose of 2 mg active ingredient.

EXAMPLE 2

600 g macrogol-15-hydroxystearate is melted. At a temperature of 50° C., 2.0 g lorazepam is added and dissolved while stirring. The clear solution is added while stirring to water for injection (WFI) Ph. Eur. (approx. 4 liters) previously heated to 50° C. and mixed. Then this mixture is diluted to exactly 5 liters with WFI to obtain an active ingredient concentration of 0.4 mg/mL.

The solution is cooled and sterile-filtered. Then glass ampoules are filled with 5 mL of the solution each and sterilized at 121° C. according to Ph. Eur. Each ampoule prepared in this way thus contains the desired therapeutic dose of 2 mg active ingredient.

EXAMPLE 3

200 g macrogol-15-hydroxystearate is melted. At a temperature of 50° C., 2.0 g lorazepam is added and dissolved while stirring. The clear solution is added while stirring to water for injection (WFI) Ph. Eur. (approx. 8 liters) previously heated to 50° C. and mixed. Next this mixture is diluted to exactly 10 liters with WFI to yield an active ingredient concentration of 0.2 mg/mL.

The solution is cooled and sterile-filtered. Then glass ampoules are filled with 10 mL of the solution in each and sterilized at 121° C. according to Ph. Eur. Each ampoule prepared in this way thus contains the desired therapeutic dose of 2 mg active ingredient.

EXAMPLE 4

500 g macrogol-15-hydroxystearate is melted. At a temperature of 50° C., 2.0 g lorazepam is added and dissolved while stirring. The clear solution is added while stirring to water for injection (WFI) Ph. Eur. (approx. 4 liters) previously heated to 50° C. and mixed. Next this mixture is diluted to exactly 2 liters with WFI to yield an active ingredient concentration of 0.4 mg/mL. The solution is cooled and sterile-filtered. Then glass ampoules are filled with 5 mL of the solution in each and sterilized at 121° C. according to Ph. Eur. Each ampoule prepared in this way thus contains the desired therapeutic dose of 2 mg active ingredient.

EXAMPLE 5

400 g macrogol-15-hydroxystearate is melted. At a temperature of 50° C., 2.0 g lormetazepam is added and dissolved while stirring. The clear solution is added while stirring to water for injection (WFI) according to Ph. Eur. (approx. 8 liters) previously heated to 50° C. Next the mixture is diluted to exactly 10 liters using water for injection to obtain an active ingredient concentration of 0.2 mg/mL.

The solution is cooled and sterile-filtered. Next glass ampoules are filled with 10 mL of the solution each and sterilized at 121° C. according to Ph. Eur. Each ampoule prepared in this way thus contains the desired therapeutic dose of 2 mg active ingredient.

EXAMPLE 6

600 g macrogol-15-hydroxystearate is melted. At a temperature of 50° C., 2.0 g lormetazepam is added and dissolved while stirring. The clear solution is added while stirring to water for injection (WFI) Ph. Eur. (approx. 4 liters) previously heated to 50° C. and mixed. Then this mixture is diluted to exactly 5 liters with WFI to obtain an active ingredient concentration of 0.4 mg/mL.

The solution is cooled and sterile-filtered. Then glass ampoules are filled with 5 mL of the solution each and sterilized at 121° C. according to Ph. Eur. Each ampoule prepared in this way thus contains the desired therapeutic dose of 2 mg active ingredient.

EXAMPLE 7

200 g macrogol-15-hydroxystearate is melted. At a temperature of 50° C., 2.0 g lormetazepam is added and dissolved while stirring. The clear solution is added while stirring to water for injection (WFI) Ph. Eur. (approx. 8 liters) previously heated to 50° C. and mixed. Next this mixture is diluted to exactly 10 liters with WFI to yield an active ingredient concentration of 0.2 mg/mL.

The solution is cooled and sterile-filtered. Then glass ampoules are filled with 10 mL of the solution in each and sterilized at 121° C. according to Ph. Eur. Each ampoule prepared in this way thus contains the desired therapeutic dose of 2 mg active ingredient.

EXAMPLE 8

500 g macrogol-15-hydroxystearate is melted. At a temperature of 50° C., 2.0 g lorazepam is added and dissolved while stirring. The clear solution is added while stirring to water for injection (WFI) Ph. Eur. (approx. 4 liters) previously heated to 50° C. and mixed. Next this mixture is diluted to exactly 2 liters with WFI to yield an active ingredient concentration of 0.4 mg/mL. The solution is cooled and sterile-filtered. Then glass ampoules are filled with 5 mL of the solution in each and sterilized at 121° C. according to Ph. Eur. Each ampoule prepared in this way thus contains the desired therapeutic dose of 2 mg active ingredient.

EXAMPLE 9

1500 g macrogol-15-hydroxystearate is melted. At a temperature of 50° C., 10.0 g oxazepam is added and dissolved while stirring. The clear solution is added while stirring to water for injection (WFI) Ph. Eur. (approx. 7 liters) previously heated to 50° C. Next the mixture is diluted to exactly 10 liters using water for injection to obtain an active ingredient concentration of 0.1 mg/mL.

The solution is cooled and sterile-filtered. Next glass ampoules are filled with 10 mL of the solution each and sterilized at 121° C. according to Ph. Eur. Each ampoule prepared in this way thus contains the desired therapeutic dose of 10 mg active ingredient.

EXAMPLE 10

2000 g macrogol-15-hydroxystearate is melted. At a temperature of 50° C., 10.0 g oxazepam is added and dissolved while stirring. The clear solution is added while stirring to water for injection (WFI) Ph. Eur. (approx. 3.5 liters) previously heated to 50° C. Next the mixture is diluted to exactly 10 liters using water for injection to obtain an active ingredient concentration of 2.0 mg/mL.

The solution is cooled and sterile-filtered. Next glass ampoules are filled with 10 mL of the solution each and sterilized at 121° C. according to Ph. Eur. Each ampoule prepared in this way thus contains the desired therapeutic dose of 10 mg active ingredient.

EXAMPLE 11

3000 g macrogol-15-hydroxystearate is melted. At a temperature of 50° C., 20.0 g oxazepam is added and dissolved while stirring. The clear solution is added while stirring to water for injection (WFI) Ph. Eur. (approx. 14 liters) previously heated to 50° C. Next the mixture is diluted to exactly 10 liters using water for injection to obtain an active ingredient concentration of 1.0 mg/mL.

The solution is cooled and sterile-filtered. Next glass ampoules are filled with 20 mL of the solution each and sterilized at 121° C. according to Ph. Eur. Each ampoule prepared in this way thus contains the desired therapeutic dose of 20 mg active ingredient.

EXAMPLE 12

2500 g macrogol-15-hydroxystearate is melted. At a temperature of 50° C., 20.0 g oxazepam is added and dissolved while stirring. The clear solution is added while stirring to water for injection (WFI) Ph. Eur. (approx. 7 liters) previously heated to 50° C. Next the mixture is diluted to exactly 10 liters using water for injection to obtain an active ingredient concentration of 2.0 mg/mL.

The solution is cooled and sterile-filtered. Next glass ampoules are filled with 10 mL of the solution each and sterilized at 121° C. according to Ph. Eur. Each ampoule prepared in this way thus contains the desired therapeutic dose of 20 mg active ingredient.

EXAMPLE 13

3000 g macrogol-15-hydroxystearate is melted. At a temperature of 50° C., 30.0 g oxazepam is added and dissolved while stirring. The clear solution is added while stirring to water for injection (WFI) Ph. Eur. (approx. 14 liters) previously heated to 50° C. Next the mixture is diluted to exactly 10 liters using water for injection to obtain an active ingredient concentration of 1.5 mg/mL.

The solution is cooled and sterile-filtered. Next glass ampoules are filled with 20 mL of the solution each and sterilized at 121° C. according to Ph. Eur. Each ampoule prepared in this way thus contains the desired therapeutic dose of 30 mg active ingredient.

EXAMPLE 14

7500 g macrogol-15-hydroxystearate is melted. At a temperature of 50° C., 50.0 g oxazepam is added and dissolved while stirring. The clear solution is added while stirring to water for injection (WFI) Ph. Eur. (approx. 40 liters) previously heated to 50° C. Next the mixture is diluted to exactly 10 liters using water for injection to obtain an active ingredient concentration of 1.0 mg/mL.

The solution is cooled and sterile-filtered. Next glass vials are filled with 50 mL of the solution each and sterilized at 121° C. according to Ph. Eur. Each vial prepared in this way thus contains the desired therapeutic dose of 50 mg active ingredient.

The invention claimed is:

1. A pharmaceutical composition in the form of an injection solution or an infusion solution, consisting essentially of:
    lormetazepam or a derivative or salts thereof;
    macrogol-15-hydroxystearate; and
    water
    said pharmaceutical composition being capable of inducing an opiate-like effect described as Straub's phenomenon.

2. The pharmaceutical composition of claim 1 wherein macrogol-15-hydroxystearate is present in an amount of 2-45 wt. %.

3. A method for inducing an opiate-like effect described as Straub's phenomenon comprising administering to a patient a pharmaceutical composition in the form of an injection solution or an infusion solution, wherein the pharmaceutical composition consists essentially of
    lormetazepam or a derivative or salts thereof;
    macrogol-15-hydroxystearate; and
    water.

4. The method of claim 3 wherein the pharmaceutical composition is administered by injection.

5. A method of using a pharmaceutical composition in the form of an injection solution or an infusion solution and consisting essentially of
    lormetazepam or a derivative or salts thereof;
    macrogol-15-hydroxystearate; and
    water
    in anesthesia, intensive care medicine, pain therapy, neurology or psychiatry by administering the pharmaceutical composition to a patient in need thereof, wherein said pharmaceutical composition being capable of inducing an opiate-like effect described as Straub's phenomenon.

6. The method of claim 5 wherein the pharmaceutical composition is administered by injection.

7. A process for preparing a pharmaceutical composition in the form of an injection solution or an infusion solution, consisting essentially of lormetazepam, macrogol-15-hydroxystearate and water for inducing an opiate-like effect described as Straub's phenomenon when injected into a patient comprising the steps of:
    regulating macrogol-15-hydroxystearate at a temperature of 40 to 60° C. in a container equipped with a stirrer,
    adding lormetazepam to the regulated macrogol-15-hydroxystearate and dissolving it while stirring at a temperature of 40 to 60° C. to form a solution,
    stirring the solution into hot water suitable for injection at 50 to 60° C., and
    cooling the solution to 20 to 30° C. while stirring.

8. A process for preparing a pharmaceutical composition in the form of an injection solution or an infusion solution, consisting essentially of lormetazepam, macrogol-15-hydroxystearate and water for inducing an opiate-like effect described as Straub's phenomenon when injected into a patient comprising the steps of:
    melting macrogol-15-hydroxystearate to form a melt;
    adding lormetazepam to said melt at a temperature of about 50° C. and dissolving the lormetazepam while stirring to form a solution;
    adding the solution to water while stirring to form an active ingredient concentration of about 0.2 mg/mL;
    cooling said solution;
    sterile filtering said solution;
    filling glass ampules with 10 mL of solution; and
    sterilizing said ampules at 121° C.;
each said ampule containing about 2 mg of active ingredient.

9. The pharmaceutical composition of claim 2 wherein macrogol-15-hydroxystearate is present in an amount of 3-10 wt. %.

* * * * *